(12) United States Patent
Friedman (10) Patent No.: US 7,390,319 B2
(45) Date of Patent: Jun. 24, 2008

(54) AUTOMATIC NEEDLE INJECTOR HAVING SAFETY TRIGGERING MECHANISM

(76) Inventor: Steven Friedman, 127 Kingston St., San Francisco, CA (US) 94110

(*) Notice: Subject to any disclaimer, the term of this patent is extended or adjusted under 35 U.S.C. 154(b) by 265 days.

(21) Appl. No.: 11/105,261

(22) Filed: Apr. 13, 2005

(65) Prior Publication Data

US 2006/0247579 A1    Nov. 2, 2006

(51) Int. Cl.
    *A61M 5/00* (2006.01)
(52) U.S. Cl. ...................................... 604/187
(58) Field of Classification Search ............. 604/187, 604/130, 131, 134, 135, 136, 137, 138, 227, 604/232, 181, 188, 192, 193, 194, 195, 197, 604/198
    See application file for complete search history.

(56) References Cited

U.S. PATENT DOCUMENTS 4,403,989 A * 9/1983 Christensen et al. ........ 604/137
5,267,963 A * 12/1993 Bachynsky ................. 604/134
5,318,522 A * 6/1994 D'Antonio .................. 604/72
5,851,197 A * 12/1998 Marano et al. ............. 604/135
6,387,078 B1  5/2002 Gillespie, III
6,530,904 B1 * 3/2003 Edwards et al. ............. 604/197

OTHER PUBLICATIONS

University of Virginia News, "U.Va. Engineering Student Says 'Nuts' to Allergies Invents Handy 'Epi-Card' for Emergencies," author unknown, Apr. 4, 2002.

* cited by examiner

*Primary Examiner*—Nicholas D. Lucchesi
*Assistant Examiner*—Christopher D Koharski
(74) *Attorney, Agent, or Firm*—Raubvogel Law Office (57) ABSTRACT

A card-shaped disposable auto-injector includes a two-step safety mechanism to prevent inadvertent use or activation of the injection mechanism. In one aspect, the auto-injector is sized and shaped so as to be easy to carry in a wallet-shaped case. In one aspect, it is rectangular in shape so as to facilitate carrying and storage, and to provide a relatively large amount of surface space for instructional text, diagrams, identifying information, warnings, and the like.

20 Claims, 11 Drawing Sheets

AUTOMATIC NEEDLE INJECTOR HAVING SAFETY TRIGGERING MECHANISM

BACKGROUND OF THE INVENTION

1. Field of the Invention

The present invention relates to devices and methods for injecting medication, and more particularly to a disposable auto-injector featuring spring activation and concealed needle, designed for one-time self-administration of medication by an individual who is not necessarily medically trained.

2. Description of the Related Art

Many individuals suffer from chronic conditions that require them to self-administer medication, either at regular intervals or in response to certain emergency conditions. For example, some people are susceptible to life-threatening allergic reactions (anaphylaxis); upon exposure to an allergen, such individuals require immediate treatment by injection of a drug such as epinephrine. There may not be time to transport the individual to a medical facility for treatment, and there may not be a medical professional nearby to administer the treatment. Indeed, it is possible that the individual may need to self-administer the drug in the event that no capable adult is nearby who can administer it to the individual.

Accordingly, a need has arisen for devices that allow easy self-administration of emergency medication. Such devices are often disposable, and are often designed to administer a pre-measured dose, so as to make them as easy as possible to use. One example of such a device is the EpiPen® epinephrine auto-injector, available from DEY L.P. of Napa, Calif. and manufactured by Meridian Medical Technologies, Inc., a subsidiary of King Pharmaceuticals, Inc. of Bristol, Tenn. Other examples include the ConfiDose™ injector by Innoject, Inc. of Athens, Tex., and the BD™ auto-injector by BD Medical Pharmaceutical Systems of Le Pont-De-Claix, France.

All of these injectors are understood to incorporate a syringe assembly within a cylindrical pen-shaped housing. Such a design carries several disadvantages which make the devices more difficult to carry, store, and use.

For example, in some situations the pen-shaped housing may make the device more difficult to carry. Users who do not have a spare pocket that fits a large, cylindrical, pen-shaped device may find it inconvenient to carry the device and may not have it with them when the need arises.

Furthermore, the pen-shaped housing offers little space for providing instructional text, diagrams, and the like. Since the users of such devices are not usually medically trained, there is a need for large, clear, prominent instructions (and warnings) including text and drawings. Conventional devices do not usually provide sufficient surface area to provide such instructions.

In addition, the pen-shaped housing can be intimidating to some users because it resembles a needle, and/or because of acquired stigma or fear associated with such devices from past usage.

Furthermore, prior art injectors often do not provide sufficient indication as to whether the injector is in safe mode or in injection-ready mode.

What is needed, therefore, is an improved auto-injector having a housing that is more conveniently shaped for users who do not have a spare pocket to carry a pen-shaped device. For example, what is needed is an auto-injector that can be carried easily in a wallet.

What is further needed is an auto-injector that provides sufficient surface area for adequate instructions including text and/or drawings.

What is further needed is an auto-injector that does not resemble a needle and that does not intimidate users.

Conventional auto-injectors carry additional disadvantages as well. For example, they typically have a limited safety mechanism that involves a one-step disengagement operation; such a safety mechanism may be inadequate to prevent inadvertent use of the device.

What is further needed is an auto-injector that addresses the above limitations and disadvantages of the prior art and that provides an improved, easier methodology for self-administering emergency injections.

SUMMARY OF THE INVENTION

The present invention is a card-shaped disposable auto-injector. The card-shaped casing provides several advantages. It is easy to carry in a wallet-shaped case; it offers a relatively large amount of surface space for instructional text, diagrams, identifying information, warnings, and the like; and it is less intimidating to some users than a pen-shaped device.

In one aspect, the injector of the present invention is specially sized and shaped to fit in a recessed cavity of a wallet-shaped travel case.

In one aspect, the injector of the present invention includes a two-step safety mechanism to prevent inadvertent use or activation of the injection mechanism.

In one aspect, the injector of the present invention provides improved visual indication as to the current state of the injector. A lever position, which is readily discernable by the user, indicates whether the injector is in a safe mode or in injection-ready mode.

BRIEF DESCRIPTION OF THE DRAWINGS

The accompanying drawings illustrate several embodiments of the invention and, together with the description, serve to explain the principles of the invention.

DETAILED DESCRIPTION OF THE EMBODIMENTS

The present invention is now described more fully with reference to the accompanying Figures, in which several embodiments of the invention are shown. The present invention may be embodied in many different forms and should not be construed as limited to the embodiments set forth herein. Rather these embodiments are provided so that this disclosure will be complete and will fully convey the invention to those skilled in the art.

In the following description, the invention is set forth in the context of a single-dose disposable auto-injector. However, one skilled in the art will recognize that the invention can be implemented in other ways as well, for example in non-disposable and/or multi-use devices. It will be apparent from the description provided herein that many other variations are possible, and that the particular embodiments set forth herein are intended to be exemplary and not limiting.

Overall Architecture

Figure 1:
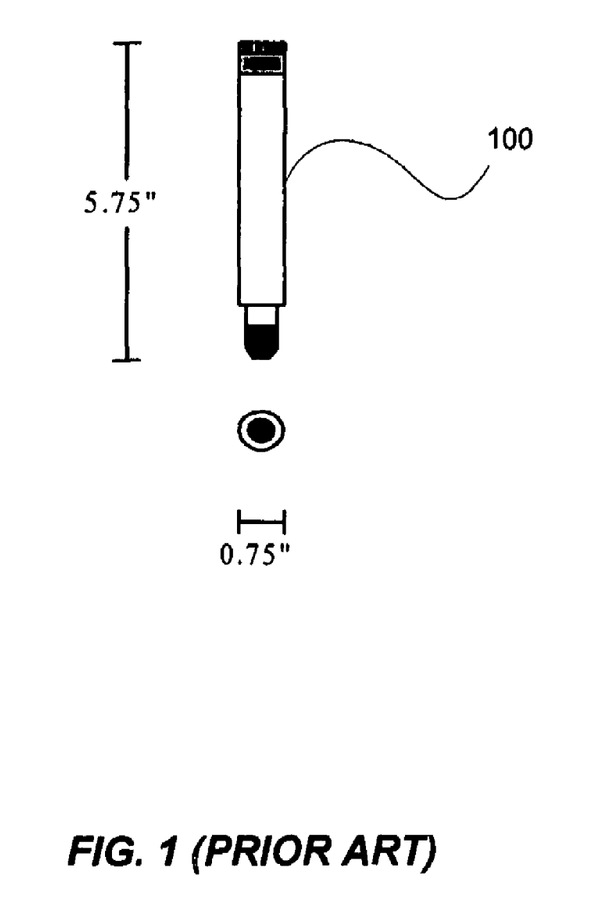
FIG. 1 depicts an injector according to the prior art.

Referring now to FIG. 1, there is shown a conventional injector 100 according to the prior art. Example dimensions for injector 100 are shown. As discussed above, injector 100 incorporates a syringe assembly within a cylindrical pen-shaped housing. This pen-shaped housing may make the device more difficult to carry, may make it difficult to provide instructional text, diagrams, and the like, and can be intimidating to some users because it resembles a needle and/or because of acquired stigma or fear associated with such devices from past usage.

Figure 3A:
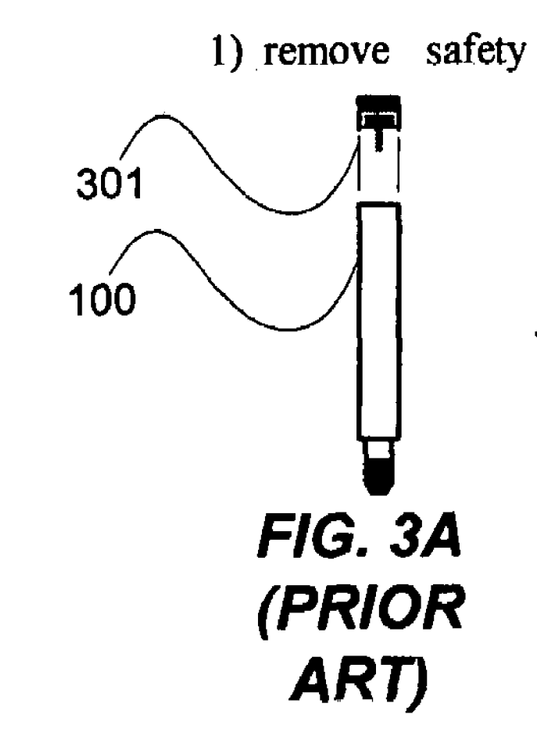
FIGS. 3A and 3B depict a one-step safety mechanism for an injector according to the prior art.
Figure 3B:
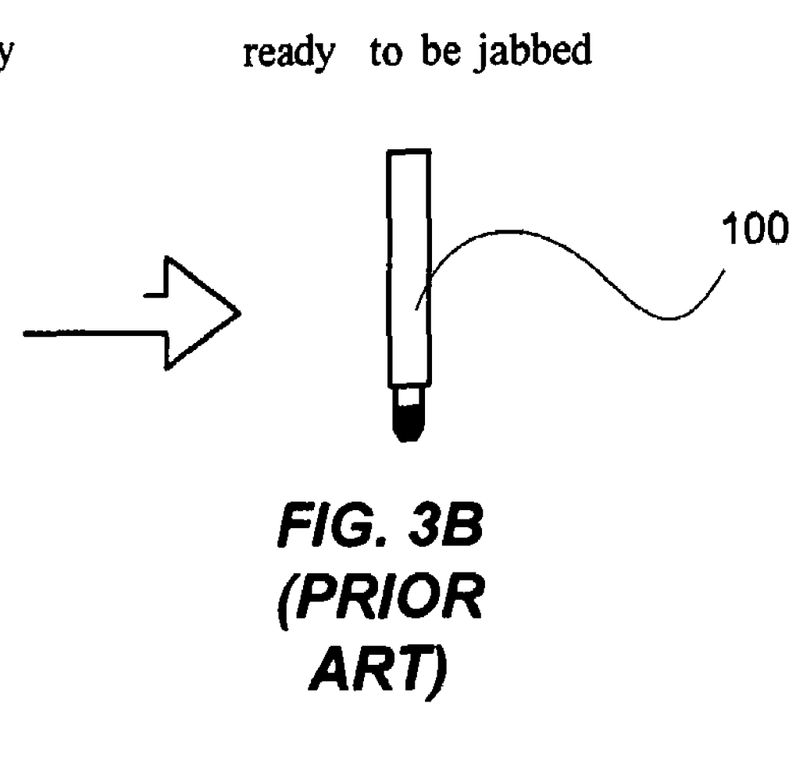

Referring now to FIGS. 3A and 3B, there is shown a one-step safety mechanism for injector 100 according to the prior art. The user removes safety 301; injector 100 is then ready for an injection, activatable by jabbing injector 100 into the injection site. As discussed above, such a safety mechanism may be inadequate to prevent inadvertent use of the injector 100.

Figure 5:
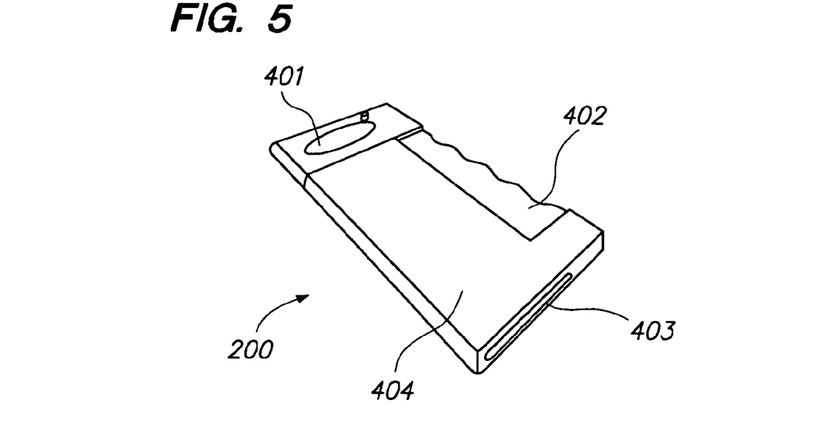
FIG. 5 is an oblique view of an injector according to one embodiment of the present invention.

Referring now to FIG. 5, there is shown an oblique view of an injector 200 according to one embodiment of the present invention.

Figure 2:
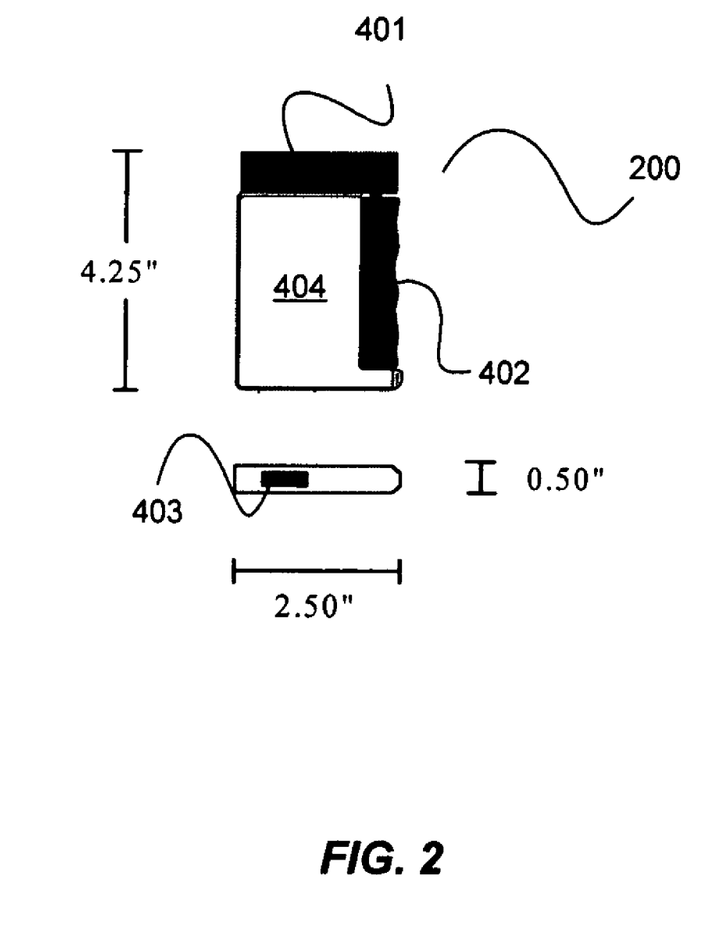
FIG. 2 is a side view and bottom view of an injector according to one embodiment of the present invention.

Referring now to FIG. 2, there is shown a side view and bottom view of injector 200 according to one embodiment of the present invention. Sample dimensions of 4.25"×2.50"×0.50" are shown, although one skilled in the art will recognize that the present invention can be implemented using dimensions and proportions other than those depicted.

Figure 9:
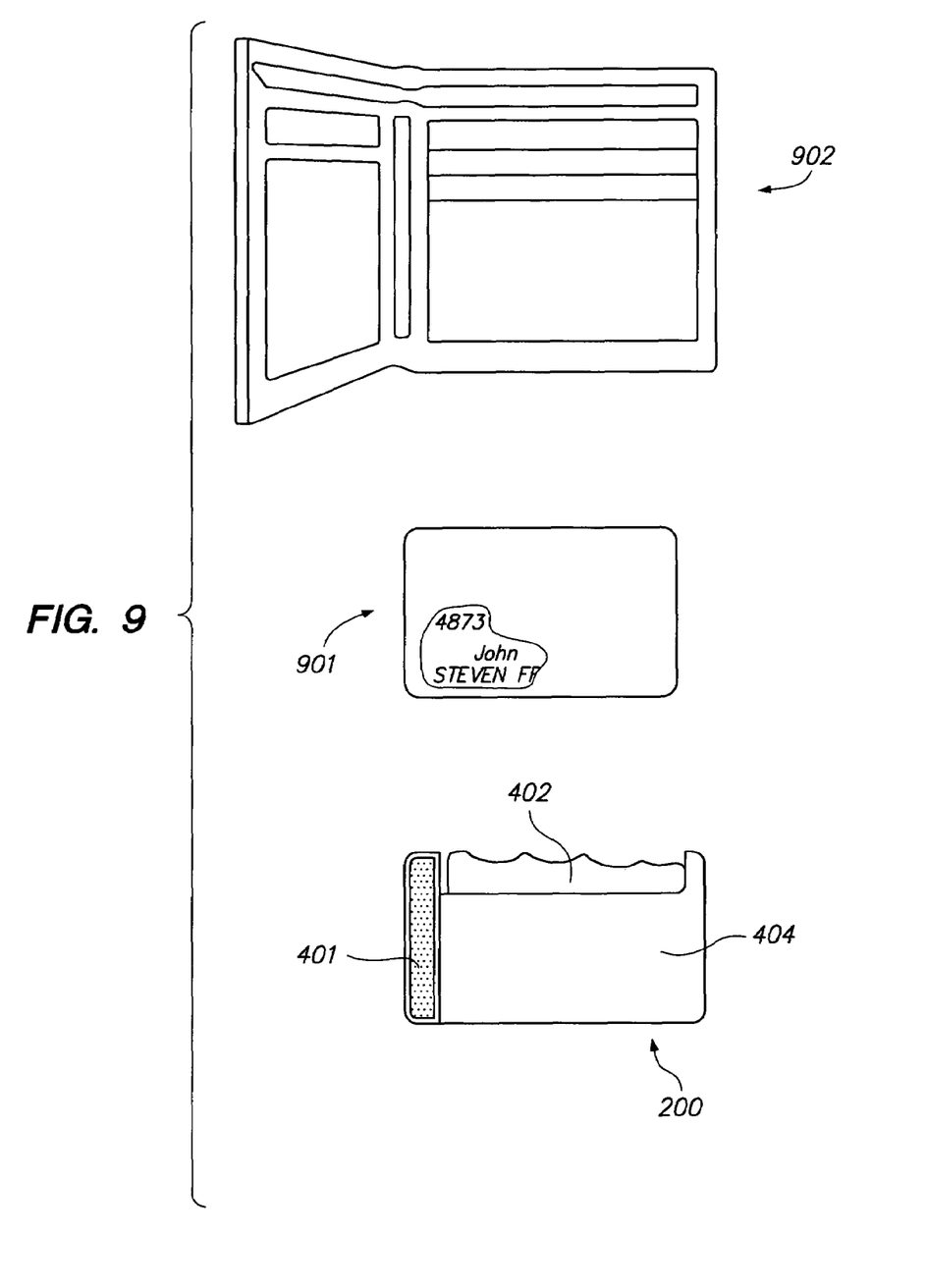
FIG. 9 is a side view of an injector according to one embodiment of the present invention, shown adjacent to a credit card for scale.

Referring now also to FIG. 9, there is shown a side view of injector 200 according to one embodiment, shown adjacent to a credit card 901 and a wallet 902 for scale.

As shown in FIGS. 2, 5, and 9, injector 200 is in one embodiment approximately credit-card-shaped and approximately credit-card sized, for more convenient transport in a wallet or similar container. In addition, such a shape offers more surface space for presenting text and/or diagrammatic instructions, expiration dates, patient information, and the like. In addition, such a shape can be less intimidating for some users because it does not resemble a needle.

In one embodiment, injector 200 includes casing 404, removable safety 401, lever 402, and trigger 403 (which is normally in a recessed position as shown in FIG. 2). Removing safety 401 and squeezing lever 402 cause trigger 403 to be activated and to protrude from casing 404, as will be described in more detail below. In one embodiment, lever 402 includes finger grooves to make it easier for a user to grip and squeeze lever 402. In one embodiment, at least one finger groove is slightly smaller than the others, to provide an intuitive affordance indicating to the user the correct orientation in which the device should be held and manipulated. Specifically, the smaller finger groove indicates the position for the user's little finger.

In one embodiment, the lever 402 position, which is readily discernable by the user, indicates whether the injector is in a safe mode or in injection-ready mode, thus providing improved indication to the user as to whether injector 200 is in safe mode or in injection-ready mode.

In one embodiment, the protruding portion trigger 403 can be smaller, or less obtrusive, than shown in the Figures, so as to assure that the bottom of casing 404 is flush against the injection site when an injection is being performed.

The particular dimensions and proportions shown in the Figures are merely exemplary. In one embodiment, relative sizes of lever 402 and trigger 403 are such that the plastic of lever 402 acts, in safe mode, as a closed door to casing opening 1202, so as to prevent or limit debris from entering casing 404.

Figure 4A:
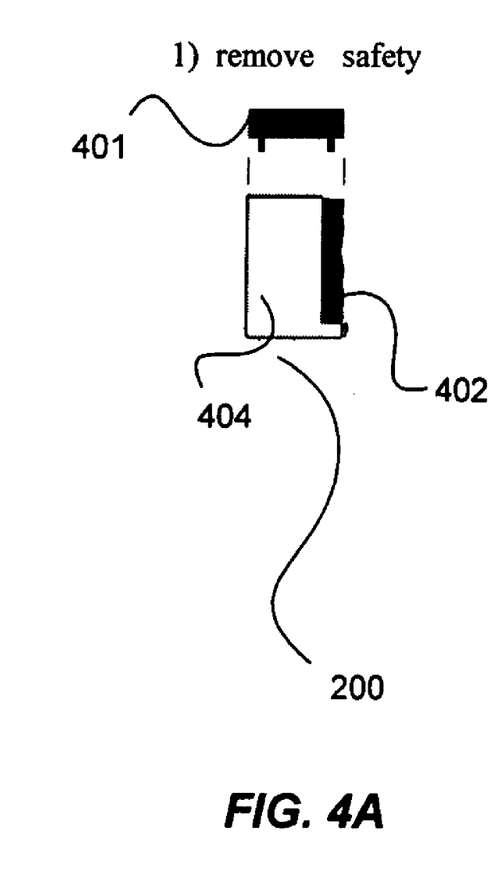
FIGS. 4A, 4B, and 4C depict a two-step safety mechanism for an injector according to one embodiment of the present invention.
Figure 4B:
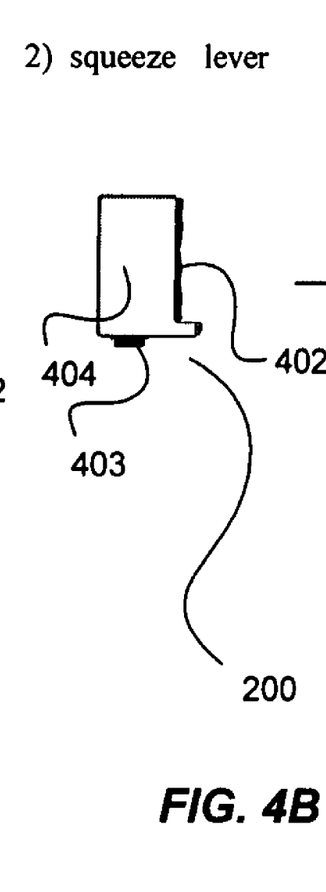
Figure 4C:
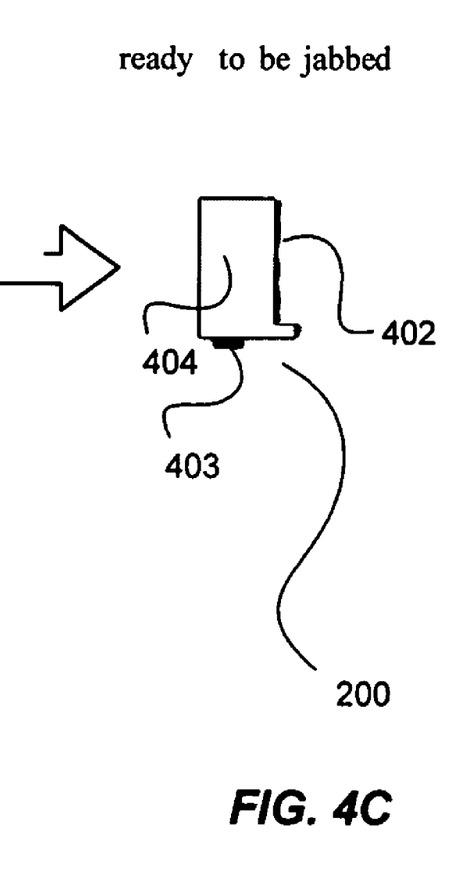
Figure 6:
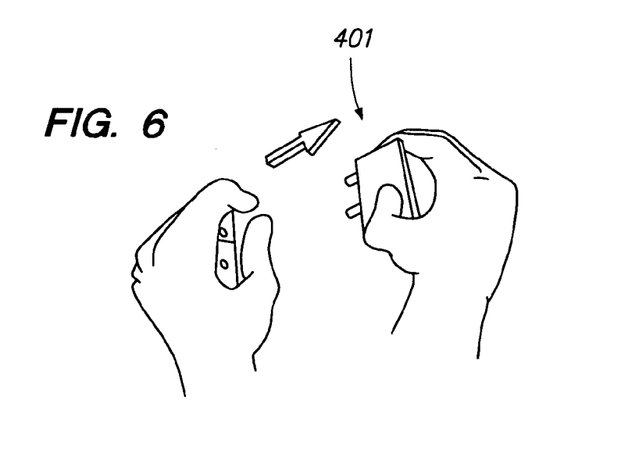
FIG. 6 depicts the step of removing a safety for an injector according to one embodiment of the present invention.

Referring now to FIGS. 4A, 4B, and 4C, there is shown a two-step safety mechanism for injector 200 according to one embodiment of the present invention. As shown in FIG. 4A, the user first removes safety 401 from casing 404. Referring also briefly to FIG. 6, there is shown the step of removing safety 401 according to one embodiment of the present invention.

Figure 7:
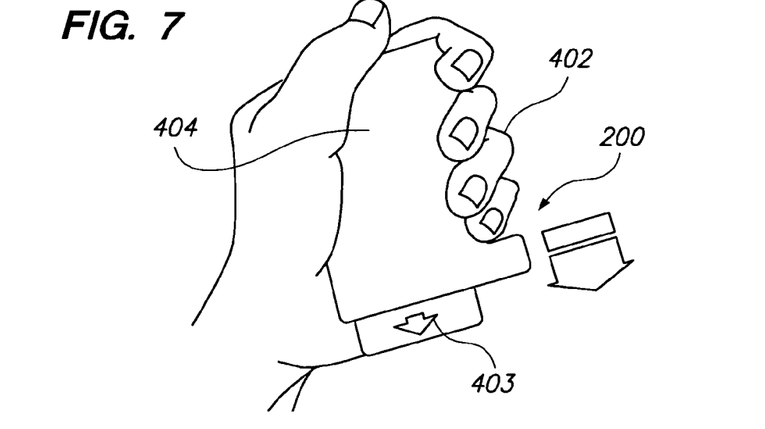
FIG. 7 depicts the step of activating a trigger for an injector according to one embodiment of the present invention.

As shown in FIG. 4B, the user then squeezes lever 402, causing trigger 403 to be activated and to protrude from casing 404. Referring also briefly to FIG. 7, there is shown the step of squeezing lever 402 (partially hidden under the hand shown in FIG. 7) to cause trigger 403 to be activated and to protrude from casing 404 according to one embodiment of the present invention.

In one embodiment, an injection take place only after safety 401 has been removed and lever 402 has been squeezed. The user can then jab injector 200 against the injection site to cause the medication to be injected.

The invention thus offers a safety feature by reducing the chance of accidental activation of the injecting mechanism. Furthermore, the user is given a sense of awareness and control by having to squeeze lever 402. In addition, casing 404 includes a lower lip that protrudes from the body of casing 404 when lever 402 is squeezed, so as to prevent the user's hand from slipping as injector 200 is jabbed.

In one embodiment, lever 402 returns to its original position if the user stops squeezing it without carrying out the injection. In another embodiment, lever 402 remains in the squeezed position unless a release mechanism (not shown) is activated. The release mechanism may be activated via a separate button, or by a brief second squeeze of lever 402.

Figure 8:
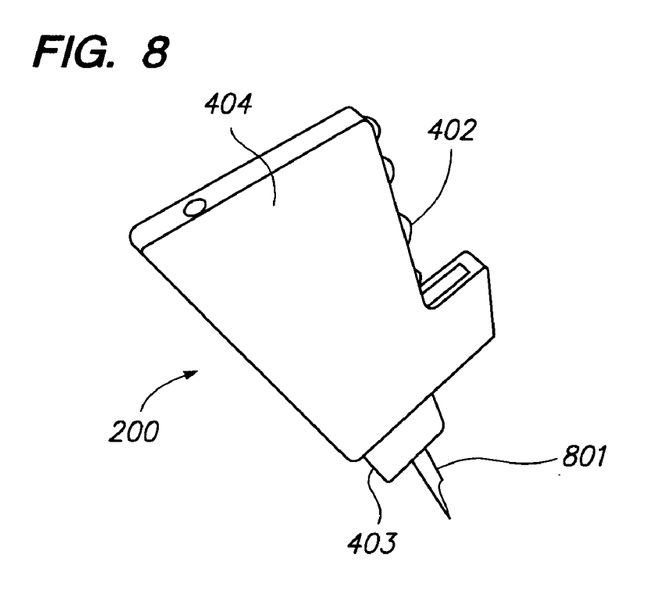
FIG. 8 depicts an injector after use, according to one embodiment of the present invention.

Referring now to FIG. 8, there is shown injector 200 after use, according to one embodiment of the present invention. Lever 402 is still in the squeezed position, and needle 801 and trigger 403 protrude from casing 404. In one embodiment, injector 200 remains in the position shown in FIG. 8 after use. In another embodiment, needle 801 and trigger 403 retract into casing 404 for safety purposes. Lever 402 may remain the squeezed position, so as to make clear the fact that the injection has been administered. In one embodiment, injector 200 cannot be reused until it has been recharged (refilled with the injectable medication); in another embodiment, injector 200 is disposable and not intended for multiple uses; in another embodiment, injector is reusable.

Figure 10:
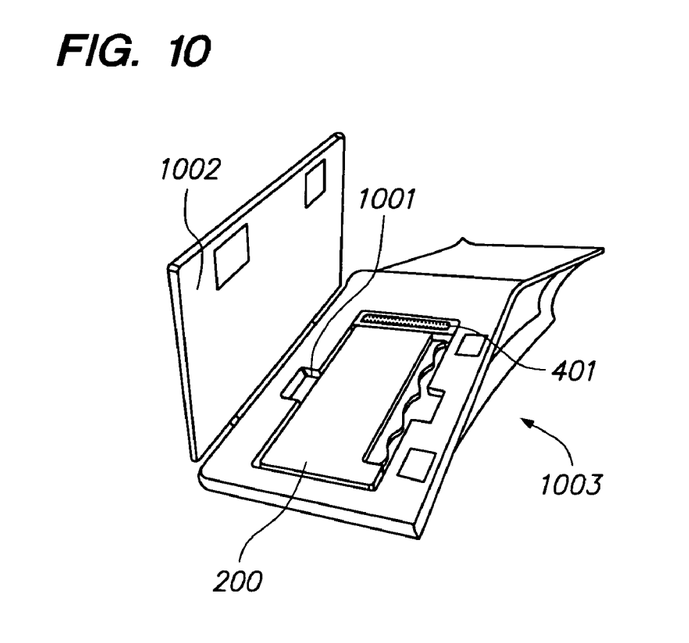
FIG. 10 depicts a travel case for carrying an injector, according to one embodiment of the present invention.

One advantage of the injector of the present invention is that it can easily be carried so that it is available at all times. Referring now to FIG. 10, there is shown travel case 1003 for carrying injector 200 according to one embodiment. Travel case 1003 is wallet-shaped and is specially designed to include embedded slot 1001 for injector 200. In one embodiment, slot 1001 has a hard cover 1002 and supported edges, ensuring that injector 200 is protected from outside stresses. Slot 1001 is designed so that, when taking injector 200 out of case 1003, only the sides of injector 200 are accessible to the user's fingers, so as to ensure that injector 200 will not be handled by safety 401. Case 1003 also offers additional space in which to articulate patient information, medication information, and instructions.

Components

Figure 11:
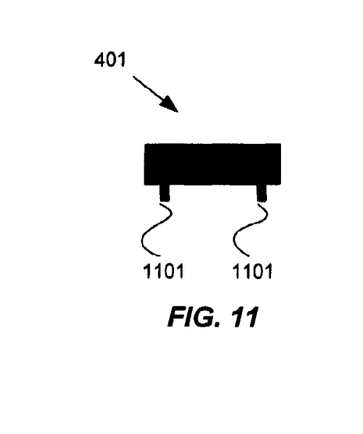
FIG. 11 is a side view of a safety for an injector, according to one embodiment of the present invention.

Referring now to FIG. 11, there is shown a side view of safety 401, according to one embodiment. In the embodiment shown, safety 401 includes prongs 1101 to fit in corresponding seats and/or openings in other components.

Figure 12:
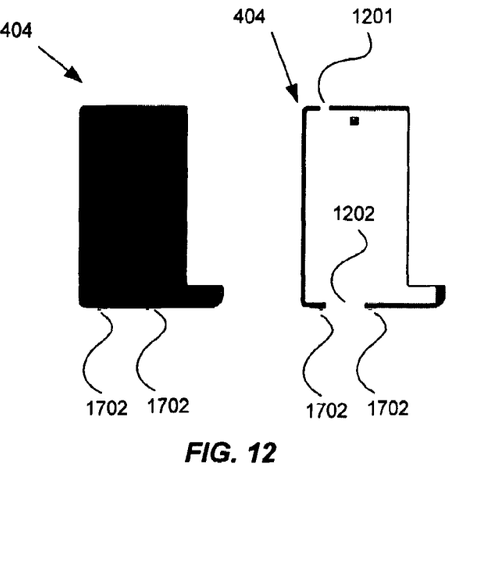
FIG. 12 is a side view of a casing for an injector, according to one embodiment of the present invention.

Referring now to FIG. 12, there is shown a side view and a cutaway view of casing 404, according to one embodiment. In the embodiment shown, casing 404 includes opening 1201 for fitting prong 1101 of safety 401. In the embodiment shown, casing 404 includes magnets 1702 for inducing trigger 403 to move into injection position through opening 1202, as will be described in more detail below.

In one embodiment, casing 404 is transparent, so that the user can see if the epinephrine (or other medication) is of the expected color and consistency. In this manner, the user can check whether the medication has not expired or has any unexpected visual characteristics. In another embodiment, casing 404 includes a transparent window to allow the user to see at least a portion of its contents. In one embodiment, text on casing 404 provides guidance as to what color to expect, and how to determine if the medication has expired based on its visual characteristics.

Figure 13:
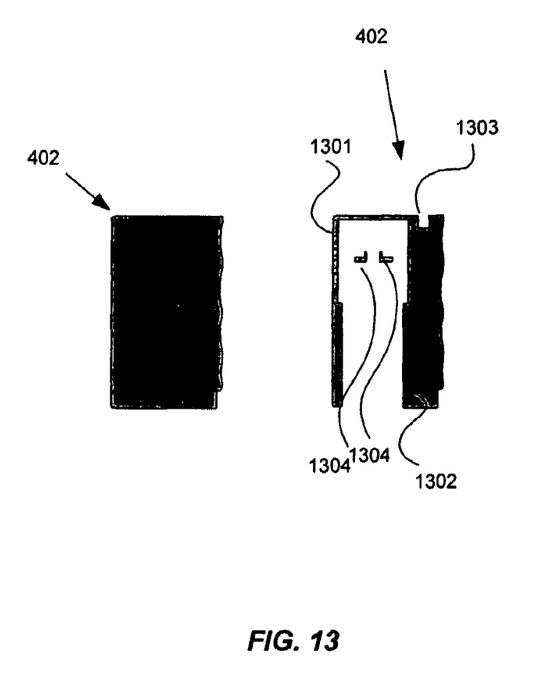
FIG. 13 is a side view of a lever for an injector, according to one embodiment of the present invention.

Referring now to FIG. 13, there is shown a side view of lever 402, according to one embodiment. In the embodiment shown, lever 402 includes brace 1301 for attachment to casing 404 and grip 1302 for the user to squeeze in order to cause trigger 403 to move into position, as will be described in more detail below. Lever 402 also includes L-shaped lever bridges 1304 for supporting spring key 1501, and opening 1303 for fitting prong 1101 of safety 401.

In one embodiment, the plastic components of injector 200 are constructed from plastic having a grade that allows for predictable, exact molds. In one embodiment, these components are constructed from polyvinyl chloride (PVC) or polypropylene, although one skilled in the art will recognize that other materials can be used. In particular, since injector 200 is designed to be carried in wallets, back pockets, and school bags, components such as casing 404 and lever 402 are, in one embodiment, constructed from a relatively strong plastic that is difficult to break, fracture, or permanently deform. At the same time, the plastic used in lever 402 is flexible enough to allow the user to squeeze lever 402 during operation of injector 200.

In one embodiment, the plastic components are constructed from plastic that is relatively strong compared to its thickness. In one embodiment, the tensile strength of the plastic components is at least 377 pounds-force/square inch, and the density of the plastic components is at least 0.05 pounds/cubic inch, although one skilled in the art will recognize that other materials can be used. In this manner, injector 200 can be constructed to be of minimum shape while still retaining sufficient strength and structural integrity to be carried and used in real-world environments.

Figure 14:
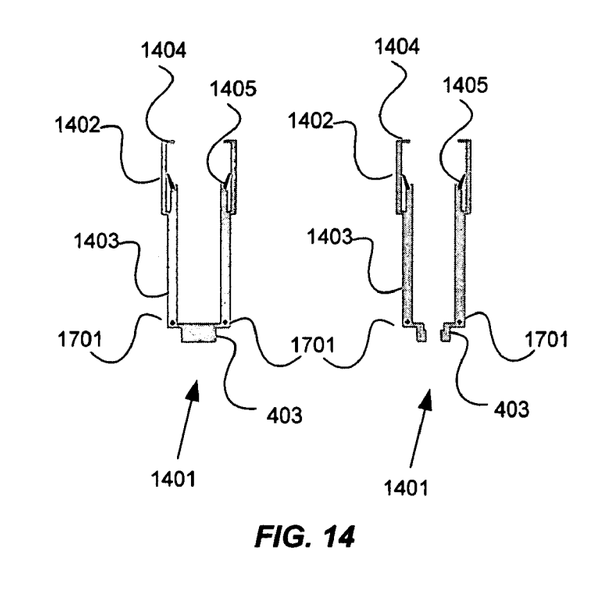
FIG. 14 is a side view of a trigger assembly for an injector, according to one embodiment of the present invention.

Referring now to FIG. 14, there is shown a side view and cutaway view of trigger assembly 1401, according to one embodiment. In the embodiment shown, trigger assembly 1401 includes:
  trigger 403,
  magnets 1701 for engagement with casing magnets 1702,
  side wall 1403 for holding syringe 1704 in place,
  seating arms 1402 (including L-shaped arm ends 1404) for ensuring that trigger assembly 1401 is snugly engaged within the space between brace 1301 and grip 1302 of lever 402, and
  torqued flippers 1405 for engaging spring key 1501.

Figure 15:
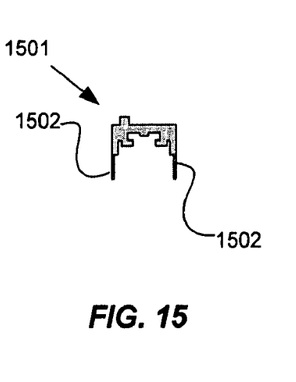
FIG. 15 is a side view of a spring key for an injector, according to one embodiment of the present invention.

Referring now to FIG. 15, there is shown a side view of spring key 1501, according to one embodiment of the present invention. In the embodiment shown, spring key 1501 includes extension arms 1502 for engagement with trigger assembly 1401.

Figure 16:
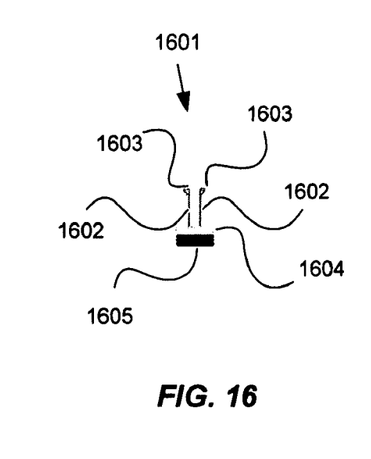
FIG. 16 is a side view of an assembly including hook hands and arms, plunger, and stopper for an injector, according to one embodiment of the present invention.

Referring now to FIG. 16, there is shown a side view of assembly 1601 including hook hands 1603 and arms 1602, plunger 1604, and stopper 1605, according to one embodiment of the present invention. Hook hands 1603 engage a cavity in spring key 1501. Plunger 1604 and stopper 1605 push syringe 1704 when an injection is being performed.

In one embodiment, hook hands 1603 and arms 1602 are constructed from metal having sufficient compression and tension strength properties, while also possessing sufficient elasticity to temporarily deform as needed. In one embodiment, these components are constructed from stainless steel.

In one embodiment, torqued flippers 1405 are relatively strong and difficult to snap, so that they can effectively distribute the user's jabbing force to spring key 1501. In one embodiment, torqued flippers 1405 are constructed from metal having sufficient elasticity to temporarily deform as needed; in another embodiment, plastic can be used. In one embodiment, these components are constructed from stainless steel, or PVC, or polypropylene.

Mechanism

As described above, in one embodiment the user performs the following steps in order to use injector 200:
  remove safety 401;
  squeeze lever 402;
  jab injector 200 into thigh or other injection site.

A mechanism for enabling the functionality of the present invention will now be described. One skilled in the art will recognize that the particular mechanism and configuration described herein is merely exemplary, and that the essential features of the invention, as set forth in the claims, can be implemented in other embodiments than that shown.

Figure 17:
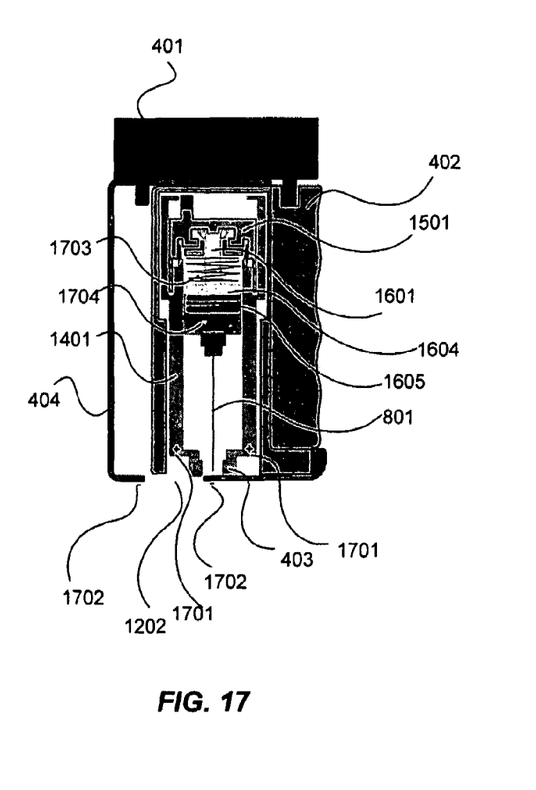
FIG. 17 is a cutaway side view of an injector, according to one embodiment of the present invention.
Figure 18:
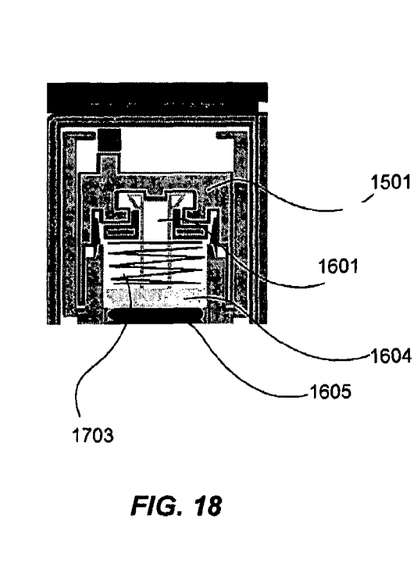
FIG. 18 is a detail of a cutaway side view of an injector, according to one embodiment of the present invention.

Referring now to FIG. 17, there is shown a cutaway side view of injector 200, according to one embodiment. The various components described above in connection with FIGS. 11 through 16 are shown. Also shown is syringe 1704 for holding the fluid to be injected, and spring 1703 for pushing plunger 1604 when an injection is being made. Referring also to FIG. 18, there is shown a detail of a cutaway side view of injector 200.

In FIGS. 17 and 18, injector is shown 200 in an initial position before safety 401 has been removed. While safety 401 is in place, lever 402 cannot move, since prongs 1101 of safety 401 are engaged in casing 404 and lever 402. Thus, trigger assembly 1401 is prevented from accidentally engaging and lowering.

Spring key 1501 is tightly nestled on the sides by trigger assembly 1401, on the bottom by lever bridges 1304, and on the top by casing 404. Spring key 1501 restrains hook hands 1603, thus preventing spring 1703 from pushing the plunger 1604. Thus, while safety 401 is in place, none of the injector components can move.

In one embodiment, syringe 1704 is rectangular with rounded edges. In one embodiment, syringe 1704 is made of glass. However, one skilled in the art will recognize that syringe 1704 may be a different shape and/or material. For example, in one alternative embodiment, syringe 1704 may be cylindrical in shape. In one embodiment, syringe 1704 is made of glass that is no thicker than $\frac{1}{8}^{th}$ of an inch.

In one embodiment, spring 1703 is rectangular. In one embodiment, spring 1703 is made of metal. However, one skilled in the art will recognize that spring 1703 may be a different shape and/or material. For example, in one alternative embodiment, spring 1703 may be cylindrical in shape and/or constructed from plastic.

Figure 19:
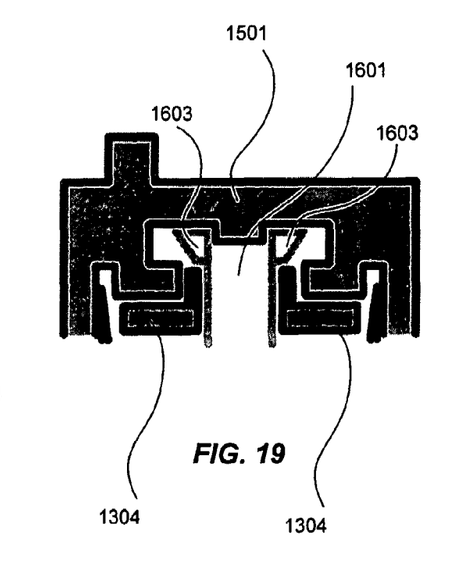
FIG. 19 is a detail of a cutaway side view of an injector, showing a mechanism by which a spring key keeps in place, and then unhooks, hook hands, according to one embodiment of the present invention.

Referring now also to FIG. 19, there is shown further detail in a cutaway view of injector 200, depicting the relationship among the various components.

Figure 20A:
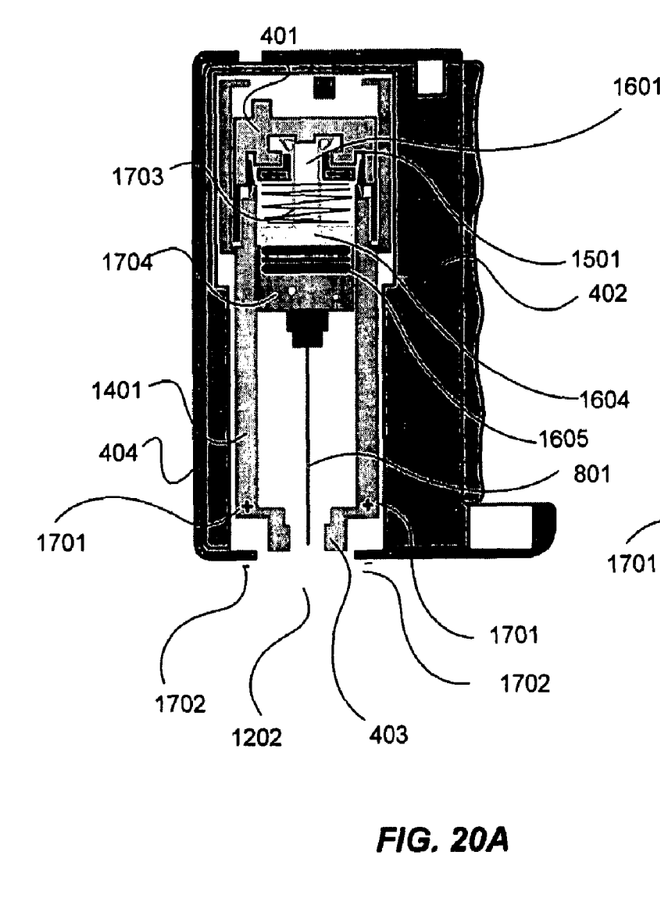
FIGS. 20A and 20B are cutaway side views of an injector, showing the operation of the trigger squeezing mechanism, according to one embodiment of the present invention.

In order to perform an injection, the user first removes safety 401. Once safety 401 has been removed, the user can squeeze lever 402. Referring now to FIG. 20A, there is shown a cutaway side view of injector 200, depicting the positioning of the internal components when lever 402 has been squeezed. Squeezing lever 402 causes trigger 403 to align with opening 1202, and also causes positive magnets 1701 and negative magnets 1702 to be positioned in the vicinity of one another. Magnets 1701 and 1702 attract one another, causing trigger 403 to move into position for injection.

The use of magnets 1701 and 1702 helps ensure that trigger 403 mates accurately with opening 1202, and that other components of the device mate with one another properly. In one embodiment, magnets are selected having strength that ensure that they do not attract one another until they are sufficiently proximate to one another, so as not to engage the device inadvertently. Magnets are advantageous because they can be calibrated to desired potentials with a high degree of accuracy.

In addition to ensuring an accurate mating, and in addition to providing an attraction force that waits for activation until its mating piece is in the vicinity, magnets 1701 and 1702 provide additional advantages. First, because magnets 1701 and 1702 can be embedded in the plastic of the components, they can serve their purposes without taking up any valuable space. Second, because their attraction becomes weaker as they get farther apart, when the user pushes trigger 403 against the injection site, it is more like breaking a seal than fighting a constant force. This provides appropriate tactile feedback to the user as to the current state of the device.

One skilled in the art will recognize that magnets 1701 and 1702 are not required, and that other mechanisms are available for coercing trigger 403 into proper position for injection. For example, weights, springs, and/or other mechanisms can be used instead of or in addition to magnets 1701 and 1702.

Figure 20B:
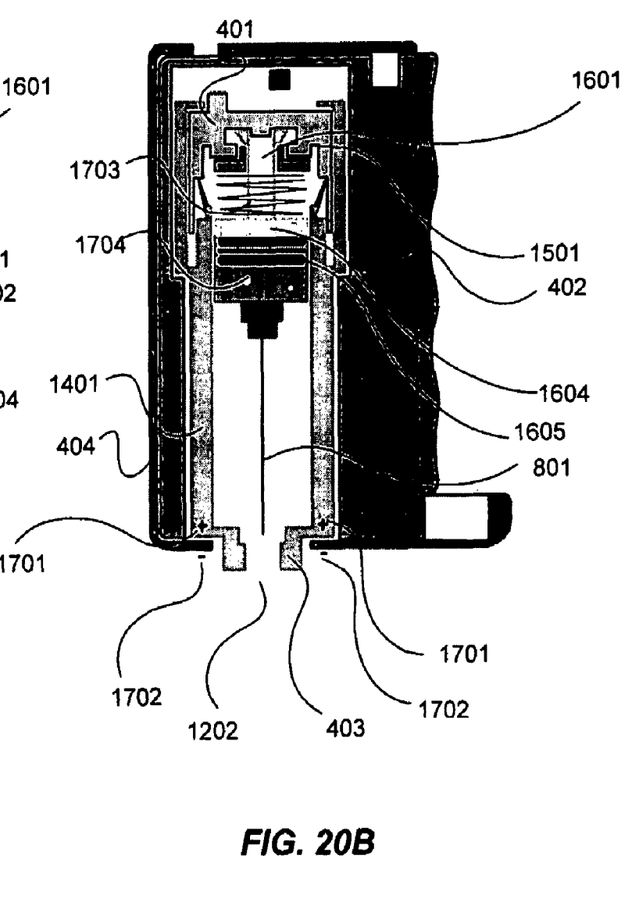

Referring now to FIG. 20B, there is shown a cutaway side view of injector 200 wherein trigger 403 has moved into position for injection. As can be seen in FIG. 20B, when trigger 403 moves into position, seating arms 1402 keep spring key 1501 in place and keep spring key 1501 bounded on all sides. Also, torqued flippers 1405 change position. Referring briefly again to FIG. 20A, the initial position of flippers 1405 is pressed against the higher stair of spring key 1501. When trigger 403 is lowered, as in FIG. 20B, torqued flippers 1405 arm themselves against the second stair of the spring key 1501. Now, when the user jabs trigger 403 against the injection site, flippers 1405 will force spring key 1501 to move up with trigger 403.

Referring again to FIG. 19, the mechanism by which spring key 1501 keeps in place, and then unhooks, hook hands 1603 is made clear. Hook hands 1603 cannot get around lever bridges 1304 because the middle of spring key 1501 keeps hands 1603 from coming together. When spring key 1501 is raised, there is no longer plastic between hook hands 1603. Also, arms 1502 of spring key 1501 (resting on lever bridges 1304), when raised, push the hypotenuses of hook hands 1603 in, enabling them to avoid bridges 1304 and unleash spring 1703.

In one embodiment, medication is delivered as follows. When spring 1703 pushes the plunger 1604, it does two things. First, plunger 1604 pushes syringe 1704 and needle 801 through casing 404. Simultaneously, though in one embodiment not as quickly, plunger 1604 pushes stopper 1605 through syringe 1704, causing medication to be forced into needle 801 before needle 801 breaks the user's skin. This ensures no air bubbles are part of the administered medication. A collar on plunger 1604 can be used to calibrate the device to stop after delivering a specified dosage.

The injector of the present invention thus includes, in various embodiments as described above and as illustrated in the FIGS., the following components:

means for holding medication, such as syringe 1704;

means for initiating transmission of the medication in response to force being applied to a bottom surface, such as trigger 403;

means for causing the means for initiating transmission to move from the safe position into the injection-ready position, such as lever 402; and means for transmitting medication into an injection site, such as needle 801;

means for assisting movement of the means for initiating transmission into the injection-ready position, such as magnets 1702; and means (which may be removable) for preventing the means for initiating transmission to move from the safe position into the injection-ready position, such as safety 401.

For example, injector 200 can be used for administering any type of medication, and is not limited to epinephrine administration. For example, injector 200 could be used for administering nerve agent antidotes; an easy-to-use and easy-to-transport injector 200 for such antidotes is an important defensive tool for front-line emergency responders and others who may be exposed to nerve agent attacks. In alternative embodiments, the present invention can be used to implement a dual cartridge injector.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

As will be understood by those familiar with the art, the invention may be embodied in other specific forms without departing from the spirit or essential characteristics thereof. For example, the particular architectures depicted above are merely exemplary of one implementation of the present invention. The functional elements and method steps described above are provided as illustrative examples of one technique for implementing the invention; one skilled in the art will recognize that many other implementations are possible without departing from the present invention as recited in the claims. Likewise, the particular capitalization or naming of the modules, protocols, features, attributes, or any other aspect is not mandatory or significant, and the mechanisms that implement the invention or its features may have different names or formats. In addition, the present invention may be implemented as a method, process, user interface, computer program product, system, apparatus, or any combination thereof. Accordingly, the disclosure of the present invention is intended to be illustrative, but not limiting, of the scope of the invention, which is set forth in the following claims.

What is claimed is:

1. An injector, comprising:
a casing having an opening;
a syringe, located within the casing, for holding medication;
a trigger, coupled to the syringe and having at least a safe position and an injection-ready position, for initiating transmission of the medication in response to a) the trigger being in injection-ready position and b) force being applied to a bottom surface of the trigger;
a lever, engaged with the casing, for causing the trigger to move from the safe position into the injection-ready position by moving the syringe in a first direction along a first axis;
a first magnet coupled to at least one of the syringe and the trigger;
a second magnet coupled to the casing; and
a needle, coupled to the syringe, for, responsive to initiation by the trigger, transmitting medication from the syringe into an injection site on a patient;
the magnets being situated to engage with one another so as to assist movement of the trigger into the injection-ready position.

2. The injector of claim 1, wherein the magnets cause at least one of the trigger and syringe to move in a second direction along a second axis substantially perpendicular to the first axis.

3. An injector, comprising:
a casing having an opening;
a syringe, located within the casing, for holding medication;
a trigger, coupled to the syringe and having at least a safe position and an injection-ready position, for initiating transmission of the medication in response to a) the trigger being in injection-ready position and b) force being applied to a bottom surface of the trigger;
a lever, engaged with the casing, for causing the trigger to move from the safe position into the injection-ready position by moving the syringe in a first direction along a first axis;
a spring coupled to at least one of the syringe and the trigger, the spring biased to assist movement of the trigger into the injection-ready position; and
a needle, coupled to the syringe, for, responsive to initiation by the trigger, transmitting medication from the syringe into an injection site on a patient;
wherein the spring causes at least one of the trigger and syringe to move in a second direction along a second axis substantially perpendicular to the first axis.

4. The injector of claim 3, further comprising:
a spring key for holding the spring; and
at least one seating arm for holding the spring key in place until trigger initiation.

5. The injector of claim 1 or 3, wherein the syringe is horizontally and vertically movable within the casing.

6. The injector of claim 1 or 3, wherein the syringe has at least a safe position and an injection-ready position.

7. The injector of claim 1 or 3, wherein the trigger is fixed in relation to the syringe.

8. The injector of claim 1 or 3, wherein the lever causes the trigger to move into the injection-ready position by moving the syringe in a first direction along a first axis.

9. The injector of claim 1 or 3, wherein:
in the safe position, the trigger is not in alignment with the opening in the casing; and
in the injection-ready position, the trigger is in alignment with the opening in the casing.

10. The injector of claim 9, wherein:
in safe position, the trigger does not protrude through the opening in the casing; and
in injection-ready position, the trigger protrudes through the opening in the casing.

11. The injector of claim 1 or 3, wherein the casing comprises two substantially rectangular surfaces and four edge surfaces.

12. The injector of claim 11, wherein the opening is located in a first edge surface of the casing.

13. The injector of claim 11, wherein each edge surface is no more than ½" in width.

14. The injector of claim 1 or 3, wherein the casing is substantially rectangular in shape.

15. The injector of claim 14, wherein the casing is no more than ½" in thickness.

16. The injector of claim 1 or 3, wherein the casing is substantially card-shaped.

17. The injector of claim 1 or 3, wherein the casing is substantially cylindrical.

18. The injector of claim 1 or 3, wherein the lever is plastic.

19. The injector of claim 1 or 3, further comprising a safety, for, when engaged with the lever, preventing the lever from being activated.

20. The injector of claim 19, wherein the safety is removable.

* * * * *